United States Patent [19]

Wile et al.

[11] Patent Number: 5,415,811
[45] Date of Patent: May 16, 1995

[54] CLEANING COMPOSITION AND METHOD FOR UTILIZING SAME

[75] Inventors: Raymond G. Wile, Liberty, Mo.; Mark E. Epstein, Olathe, Kans.

[73] Assignee: E and R Investments, Kansas City, Kans.

[21] Appl. No.: 193,564

[22] Filed: Feb. 8, 1994

Related U.S. Application Data

[63] Continuation of Ser. No. 71,317, Jun. 2, 1993, abandoned, which is a continuation of Ser. No. 682,646, Apr. 9, 1991, abandoned.

[51] Int. Cl.$^6$ ............................................. C07C 51/54
[52] U.S. Cl. ........................... 252/546; 252/170; 252/171; 252/153; 252/DIG. 10
[58] Field of Search ............... 252/DIG. 10, 170, 153, 252/545, 546, 171

[56] References Cited

U.S. PATENT DOCUMENTS

| | | | |
|---|---|---|---|
| 4,299,749 | 11/1981 | McCarthy | 260/29.67 |
| 4,302,348 | 11/1981 | Requejo | 252/135 |
| 4,315,828 | 2/1982 | Church | 252/153 |
| 4,397,913 | 8/1993 | Fahey | 106/211 |

OTHER PUBLICATIONS

*Fluorad Brand Fluorochemical Surfactants*, Product of 3M Company, 1968.
*Introducing Unique New Monflor*, Imperial Chemical Industries, Ltd.(No Date).
STN—File "Registry" of Registry No. 2991-51-7, 1992.

*Primary Examiner*—Michael Lewis
*Assistant Examiner*—Thomas G. Dunn, Jr.
*Attorney, Agent, or Firm*—J. David Wharton; Shook, Hardy & Bacon

[57] ABSTRACT

An aqueous cleaning composition useful for cleaning hard surfaces such as glass, and a method for utilizing same, wherein relatively no residue is formed by the composition upon application to the surface. The composition comprises an aqueous mixture of an alcohol, a glycol ether, and a surfactant, wherein the surfactant is a fluorosurfactant present in an amount equal to or less than 40 parts per million, preferably 30 parts per million, based on the total composition.

9 Claims, No Drawings

CLEANING COMPOSITION AND METHOD FOR UTILIZING SAME

This is a continuation of application Ser. No. 08/071,317 filed on Jun. 2, 1993 (now abandoned), which is a continuation of Ser. No. 07/682,646, filed on Apr. 9, 1991 (now abandoned).

BACKGROUND AND SUMMARY OF THE INVENTION

This invention relates in general to a cleaning composition, and more particularly relates to a composition useful for cleaning hard surfaces, such as a glass surface, wherein the composition leaves relatively no residue upon the hard surface when applied.

Aqueous cleaning compositions of the type comprising a combined alcohol and glycol solvent system, a surface active agent, and ammonia have proven particularly useful for cleaning glass or other similar hard surfaces. Various improvements in the cleaning effectiveness of these compositions have been suggested over the years. For example a heavy duty cleaning composition is provided by incorporating a detergent such as an alkali metal polyphosphate (U.S. Pat. No. 3,464,735 to Stonebreaker, et al.) or a polyacrylic resin (U.S. Pat. No. 4,606,842 to Keyes, et al.) into the aqueous composition. For lighter cleaning, sulfonated fatty alcohols in the form of the alkali metal salts thereof, such as sodium laurel sulfate, have typically been utilized as surfactants in the aqueous cleaning compositions. Aside from acting as wetting agents, the sulfonate surfactants impart detergency characteristics for improved cleaning capacity.

As a result of these improvements, cleaning compositions are now available that can remove substantial amounts of heavy duty dirt and grease deposits. However, for general cleaning purposes the presence of streaks and spots left on the surface after being cleaned significantly detracts from its final overall appearance. It is known that the cleaning compositions heretofore mentioned leave a dry residue on the substrate if applied and allowed to remain on the glass or other hard surface for some period of time. Even though the surface to be cleaned is generally wiped following the application of a cleaning composition, it has proven difficult to wipe the surface clean so that all of the composition is removed. Consequently, the presence of the cleaning composition and corresponding residue on the glass or other similar hard surface causes unacceptable streaking and spotting.

Therefore, it is a primary objective of the present invention to provide a cleaning composition useful for cleaning hard surfaces, such as glass, that leaves relatively no residue upon the surface following application.

Another object of the present invention is to provide a cleaning composition useful for cleaning hard surfaces, such as glass, that can be removed quickly without excessive wiping.

A further object of the present invention is to provide a cleaning composition having sufficient wettability and foaming action to effectively clean the entire hard surface on which it is applied.

It is also an object of the present invention to provide a method for cleaning hard surfaces such as glass wherein the hard surface is effectively cleaned and relatively no residue, streaks or spots appear on the surface.

The inventors have discovered that a very effective composition for cleaning hard surfaces such as glass is provided by an aqueous mixture of a lower alcohol, a glycol ether, ammonia and a surfactant, wherein the surfactant is a fluorosurfactant present in amounts equal to or less than about 40 parts per million (by weight) and preferably equal to or less than about 30 parts per million (by weight), relative to the total composition. Prior compositions generally include much higher amounts of surfactant as it was thought that a relatively high concentration of surfactant was necessary to achieve adequate cleaning. Following the teachings of the prior art, if additional "cleaning power" was desired, the amount of surfactant was increased, rather than decreased, as contemplated by the percent invention.

DETAILED DISCLOSURE OF THE INVENTION

The glass or other similar hard surface cleaning composition of the present invention is an aqueous mixture comprising an alcohol, a glycol ether, ammonia, and a surfactant, wherein the surfactant is a fluorosurfactant present in amounts equal to or less than 40 parts per million (ppm), and preferably equal to or less than 30 ppm (by weight). Other conventional ingredients such as perfumes, anti-fog agents, foaming agents and propellants can be added in amounts that do not adversely affect the beneficial properties of the invention composition by adding substantial residue particles.

The lower alliphatic alcohols are particularly suitable as the alcohol component, wherein specially denatured lower alcohols are preferred. Any lower alcohol having from 2 to 5 carbons can be utilized such as propanol, ethanol, isopropanol, methanol and mixtures thereof. An improved composition is prepared by utilizing ethanol as the alcohol component. The ethanol flash dries and evaporates quickly to provide a cleaning composition that is easily removed with very little wiping. Therefore the ethanol composition is less likely to streak or show spots. For commercial purposes, an amount of methanol is also suggested as a denaturate to protect consumers. A suitable amount of the lower alcohol is about 1 to 40% by weight, preferably about 5 to 30% by weight, and most preferably about 10 to 25% by weight, based on the total composition. The most preferred alcohol component comprises a mixture of methanol and ethanol, wherein the amount of methanol ranges from 0.5 to 10% by weight of the total composition with the balance of the total alcohol component being ethanol.

The glycol component can comprise any glycol having from 2 to 6 carbons, wherein the glycol ethers are preferred. Suitable glycol ethers include dipropylene glycol methyl ether, diethylene glycol methyl ether, diethylene glycol ethyl ether, diethylene glycol propyl ether, ethylene glycol propyl ether, ethylene glycol monobutyl ether, and propylene glycol tertiary butyl ether, wherein ethylene glycol monobutyl ether, and propylene glycol tertiary butyl ether are preferred. The amount of the glycol present is generally in the range from about 1 to 15% by weight, preferably 2 to 10% by weight and most preferably 3 to 6% by weight, based on the total composition. Mixtures of two or more of the glycols may be employed within these weight ranges.

It is also preferred to incorporate ammonia in the aqueous cleaning composition of the invention as a fugitive agent that inhibits corrosion and also serves as a wetting agent. Preferably the ammonia is provided as an aqueous solution of ammonia such as a 45% (by volume) ammonia solution. Suitable amounts of the ammonia in the formulation of the present invention are in the range of about 0.05 to 0.15%, preferably 0.01 to 0.5% by weight based on the total composition.

The fluorocarbon surfactant is provided in an amount equal to or less than about 40 ppm or about 0.004% by weight active solids in the composition, and preferably equal to or less than about 30 ppm or about 0.003% by weight active solids in the composition. The applicant has discovered that the class of compounds known as fluorocarbon surfactants are particularly useful for this invention because of their ability to lower surface tension and enhance wettability and foam stability at concentrations much lower than was previously thought to be effective. Water soluble anionic, non-ionic and cationic fluorocarbon surfactants are preferred, and anionic fluorosurfactants are most preferred. Particularly suitable surfactants for purposes of the present invention include potassium fluoroalkyl carboxylates. An example of this preferred class of fluorocarbon surfactants can be represented by the following formula:

Another example of a suitable anionic fluorosurfactant is represented generally by the following formula:

$(R_fCH_2CH_2O)P(O)(ONH_4)_2$ where $R_f$ is equal to $F[CF_2CF_2]_{3-8}$.

Especially preferred results have been obtained with the potassium fluoralkyl carboxylate sold under the trademark Florad FC-129 from 3M Industrial Chemical Products.

The composition may, of course, include other conventional adjuvants commonly used in hard surface cleaning compositions that do not add a substantial amount of residual material. Fragrance can be added in amounts ranging from 0.01 to 0.1% (by weight) with little negative consequence.

In addition to the ingredients named above, the water provided to form the aqueous solution is preferably soft deionized water having a hardness, i.e. mineral content, of less than about 100 ppm, preferably no more than 50 ppm and most preferably no more than 30 ppm (all by weight).

The formulation may be applied simply as a solution by wiping it on the surface to be cleaned, or the container may also have an atomizer attachment for spraying on the surface. Aerosol formulas can be provided with conventional propellants such as propane, butane, or a fluorocarbon. Following application of the composition, the surface is wiped with a clean cloth or towel until dry.

In preparing the composition of the present invention, it is most preferable to use a dedicated mixing tank to prevent contamination of the cleaning composition. The mixing tank is charged with deionized water and the glycol ether, alcohol, surfactant, fragrance and ammonia. The final composition results after mixing at room temperature for about 15 minutes.

A general formula for the composition according to the present invention is set forth in Example 1 below:

EXAMPLE 1

| Ingredient | Percent by Weight |
| --- | --- |
| Denatured Ethanol | 19.0 |
| Ethylene Glycol Monobutyl Ether | 4.0 |
| Fluorosurfactant[1] | .004 |
| Deionized water | 76.996 |

A preferred formulation is set forth in Example 2 below:

EXAMPLE 2

| Ingredient | Percent by Weight |
| --- | --- |
| Denatured Ethanol | 19.0 |
| Ethylene Glycol Monobutyl Ether | 4.0 |
| 45% Ammonia Solution | 0.1 |
| Fluorosurfactant[1] | .006 |
| Fragrance[2] | .04 |
| Deionized water | 76.854 |

[1]FC-129 anionic surfactant available from 3M Industrial Chemical Products Division, St. Paul, Minnesota having a 50% (by weight) active ingredient in a solvent comprising 2-butoxyethanol, ethyl alcohol and water.
[2]L4873 fragrance provided by Arylessence, Inc., Marietta, Georgia.

Having thus described the invention, we claim:

1. An aqueous cleaning composition comprising 1–40% by weight of an alcohol, 1–15% by weight of a glycol ether a surfactant, and the balance water, wherein said surfactant is a fluorosurfactant present in an amount equal to about 30 parts per million by weight of the total composition, and wherein the fluorosurfactant is a potassium fluoroalkyl carboxylate.

2. An aqueous cleaning composition according to claim 1 further comprising ammonia.

3. An aqueous cleaning composition according to claim 1 wherein said alcohol is an alliphatic lower alcohol having from two to six carbons atoms.

4. An aqueous cleaning composition according to claim 3 wherein said alcohol is selected from one or more of the following: propanol, ethanol, isopropanol, methanol, and mixtures thereof.

5. An aqueous cleaning composition according to claim 4 wherein said alcohol is ethanol.

6. An aqueous cleaning composition according to claim 1 wherein said glycol ether is selected from the group consisting of: ethylene glycol monobutyl ether and propylene glycol tertiary butyl ether and mixtures thereof.

7. An aqueous cleaning composition according to claim 7 wherein said fluorosurfactant has the following formula:

8. An aqueous cleaning composition according to claim 1 wherein said aqueous cleaning composition comprises soft water having a hardness of less than 100 parts per million of the total composition.

9. An aqueous cleaning composition according to claim 8 further comprising ammonia.

* * * * *